United States Patent [19]

Holoff, deceased et al.

[11] Patent Number: 4,524,647
[45] Date of Patent: Jun. 25, 1985

[54] TWEEZER ASSEMBLY

[76] Inventors: Manning Holoff, deceased, late of Los Angeles, Calif.; by Geraldine Holoff, executrix, 2340 Donella Cir., Los Angeles, Calif. 90077

[21] Appl. No.: 432,190

[22] Filed: Oct. 1, 1982

[51] Int. Cl.³ .................................................. B25B 9/02
[52] U.S. Cl. ...................................... 294;99.2; 128/354
[58] Field of Search ................... 81/43; 128/354, 355; 294/99 R; D24/24; D8/54, 57

[56] References Cited

U.S. PATENT DOCUMENTS

| 2,376,448 | 5/1945 | Neugass | 81/43 |
| 2,435,741 | 2/1948 | Fleenor | 81/43 |
| 2,666,843 | 1/1954 | Zuckerman | 128/354 |
| 3,287,547 | 11/1966 | Speeding | 128/354 |

FOREIGN PATENT DOCUMENTS 85614  5/1955  Norway ................................ 81/43

Primary Examiner—Roscoe V. Parker
Attorney, Agent, or Firm—Lyon & Lyon

[57] ABSTRACT

A tweezer assembly for handling small objects comprising a housing, a magnifying lens, a light source and tweezers. The tweezers are pivotally mounted on the housing such that the gripping ends thereof can be pivoted into the focal range of the magnifying lens which in turns lies within the path of illumination of the light source. The assembly is configured so as to allow the user with one hand to grip the assembly housing, activate the light source and operate the tweezers on an object which, with the ends of the tweezers, is both magnified and illuminated.

2 Claims, 4 Drawing Figures

TWEEZER ASSEMBLY

BACKGROUND OF THE INVENTION

The present invention relates to a compact tweezer assembly which is operable with one hand and provides both illumination and magnification of the ends of the tweezers.

Tweezers are used for a wide variety of applications. In the home, they are used to remove splinters embedded in one's skin. They are also used in certain repair work, model building, stamp collecting and other endeavors involving the handling of small items. Tweezers also have a myriad of industrial applications where small articles must be handled with precision. For example, in numerous mechanical assembly operations such as watch malcing and repair tweezers are needed to handle and position the small parts for assembly work. In each application, the item being handled is generally quite small making visibility an inherent problem. The tweezer assembly disclosed herein helps significantly to solve this problem and does so without adversely affecting the ability of the user to manipulate the tweezers with a single hand.

SUMMARY OF THE INVENTION

Briefly, the present invention comprises a compact tweezer assembly which is operable with a single hand and which provides illumination and magnification of the ends of the tweezer and any object carried thereby to facilitate gripping and handling of the object by the tweezers.

It is the primary object of the present invention to provide a pair of tweezers with means secured thereto for illuminating and magnifying the ends of the tweezers without adversely affecting the ability of one to operate the tweezers with a single hand.

This and other objects and advantages of the present invention will become apparent from the following detailed description taken in conjunction with the accompanying drawings.

IN THE DRAWINGS

DESCRIPTION OF THE PREFERRED EMBODIMENT

Figure 1:
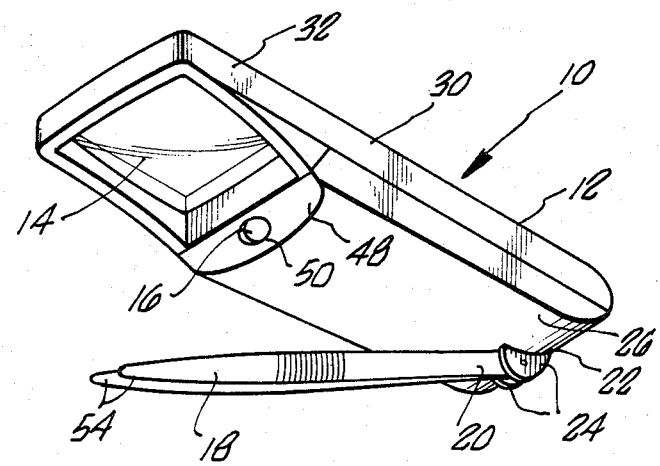
FIG. 1 is a perspective view of the present invention.

Referring now in detail to the drawings, the tweezer assembly 10 comprises a body portion 12, a magnifying lens 14, a light source 16 and tweezers 18. The tweezers 18 are pivotally secured at their joined rearward end 20 to the underside of the body portion of the assembly adjacent the rearward end 22 thereof. In the preferred embodiment illustrated in the drawings, this pivotal mounting is provided by a pair of ears 24 which are formed with the underside 26 of the body portion, project therefrom and are spaced a distance apart approximately equal to the thickness of the base 20 of the tweezers. The tweezers are then pivotally secured to ears 24 by a pin 28 extending through the ears and the base of the tweezers.

The body portion 12 of the tweezer assembly, absent ears 24, and including lens 14 and light source 16, have been manufactured and sold in the past as a reading aid by Manning-Holoff Company under the name Magna-Lite which is a registered trademark of Manning-Holoff Company. As seen in the drawings, the body portion 12 is comprised of an upper cover 30 and lower cover 26 which define a lens holding frame 32 and an interior chamber 34 for the mounting of the batteries 36 therein against contacts 38 and 40. The upper cover 30 defines a raised portion 42 for the mounting of an actuating button 44 for the selective activation light source 16 which is also mounted within chamber 34 by an electrically conductive mounting bracket 46. The actuating button 44 is of a conventional locking type so that the button can be depressed to activate light source and if desired, pushed forwardly, to lock the button in the "on" position. The underside 26 of the body portion 12 has an inclined forward edge portion 48 with a centrally disposed aperture 50 therein for directing the beam of illumination from light source 16 into the focal range of magnifying lens 14. The underside 26 and upper cover 30 of the body portion are secured together by a snap fit and a recess 52 is defined thereby in the rearward end of the body portion for the insertion of a coil or similar object to effect separation of the upper and underside of the body portion for the replacement of the batteries 36 and/or light source 16.

Figure 2:
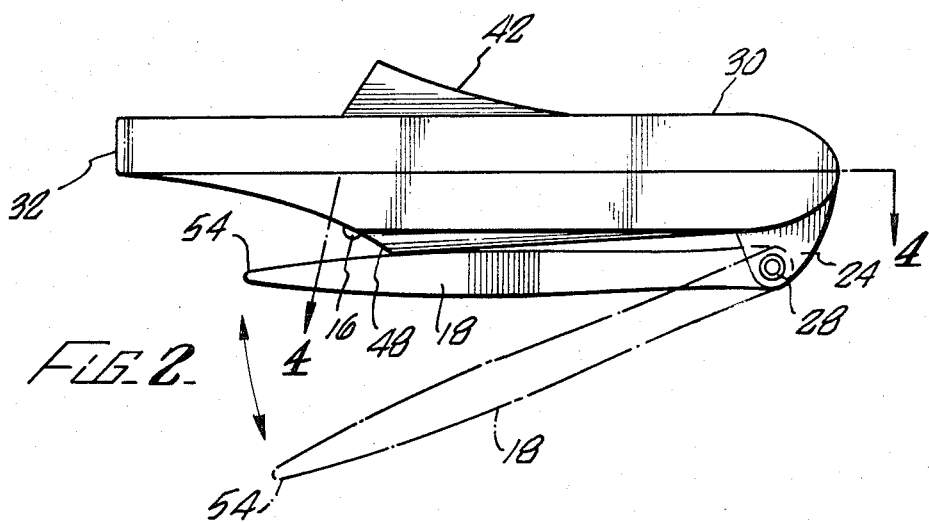
FIG. 2 is a side view of the tweezer assembly of the present invention illustrating the pivotal movement of the tweezers with respect to the assembly housing.
Figure 3:
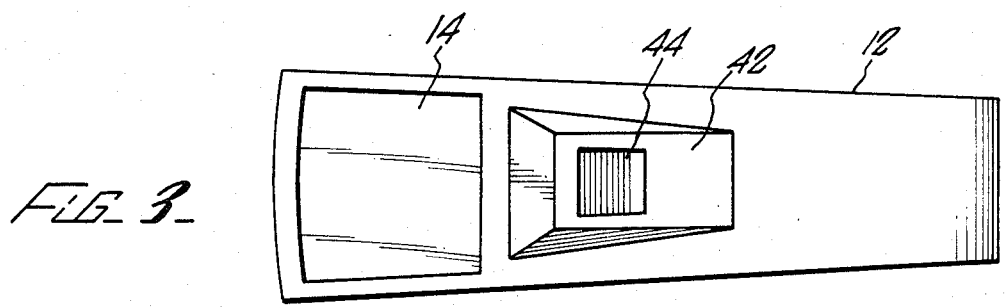
FIG. 3 is a top view of the tweezer assembly of the present invention.
Figure 4:
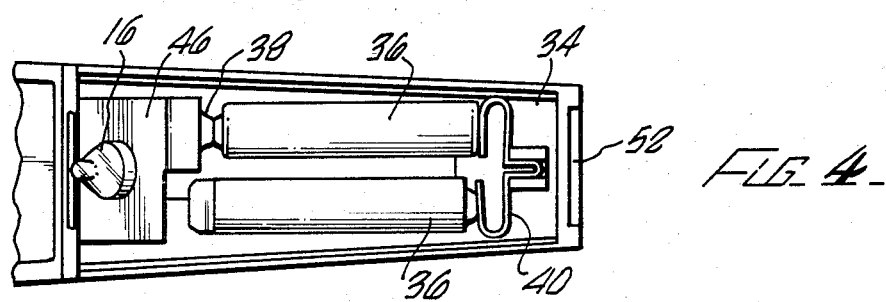
FIG. 4 is a bottom view of a portion of the tweezer assembly with the cover removed illustrating the light and power sources of the assembly.

The pivotal mounting of the tweezers 18 allow the tweezers to be disposed adjacent the underside 26 of the body portion 12 for storage convenience as illustrated in FIG. 2. In use, the tweezers 18 are pivoted downwardly from the body portion as illustrated in the phantom lines in FIG. 2 to bring the gripping ends 54 of tweezers 18 concurrently into the focal range of magnifying lens 14 and the path of illumination of light source 16. As used herein the term focal range means that distance within which the magnified object is in focus. While this varies depending on the shape of the lense being used and, theoretically the object is in focus only at the focal point of the lense, there exists a limited range of about two inches within which the magnified item is in acceptable focus for practical use.

Because of the structural relationship between the body position 12 and tweezers 18, one can activate light source 16 by button 44 and easily control the body portion 12 of the assembly in the palm of the hand while precisely manipulating the tweezers 18 with the thumb and forefinger of the same hand. The cooperation and coordination of the beam of light eminating from light source 16 through the focal range of lens 14 and the positioning of the ends 54 of tweezers 18 in the area of intersection of the light beam and focal range provides excellent illumination and magnification of the ends of the tweezers and any objects carried thereby to greatly facilitate the use of the tweezers in handling small objects.

Various changes and modifications may be made in carrying out the present invention. Insofar as these changes and modifications are within the purview of the appended claims, they are to be considered as part of the invention.

I claim:

1. A tweezer assembly comprising a body portion, a magnifying lens carried by said body portion adjacent one end thereof and defining a given focal range, a light source carried by said body portion and positioned such that the path of illumination eminating therefrom passes through said focal range, means for activating said light source, and a pair of tweezers, one end of said tweezers being pivotally mounted on said body portion such that the other extended gripping ends of said tweezers are moveable between a storage position adjacent said body portion and an operative position within the focal range of said lens and the path of illumination of said light source wherein the ends of said tweezers are concurrently magnified and illuminated to facilitate visibility thereof.

2. A tweezer assembly adapted to be held and manipulated by one hand of the user, said assembly comprising an elongated body member defining a lens securement from adjacent one end thereof and a handle portion extending from said frame, a magnifying lens carried within said securement frame and defining a given focal range, a light source carried by said handle portion and positioned such that the path of illumination eminating therefrom passes therethrough said focal range, means carried by said handle portion for activating said light source, a pair of ears projecting from said handle portion of said body member adjacent one end thereof, and a pair of tweezers, one end of said tweezers being pivotally mounted between said ears such that the other extended gripping ends of said tweezers can be selectively pivoted from a first storage position adjacent said body portion to a desired operative position wherein the gripping ends of said tweezers are concurrently disposed within the focal range of said lens and the path of illumination of said light source whereby the ends of said tweezers are concurrently magnified and illuminated to facilitate visibility thereof.

* * * * *